United States Patent [19]

Grimes

[11] 4,414,537
[45] Nov. 8, 1983

[54] DIGITAL DATA ENTRY GLOVE INTERFACE DEVICE

[75] Inventor: Gary J. Grimes, Thornton, Colo.

[73] Assignee: Bell Telephone Laboratories, Incorporated, Murray Hill, N.J.

[21] Appl. No.: 302,700

[22] Filed: Sep. 15, 1981

[51] Int. Cl.³ ............................................. G06F 3/02
[52] U.S. Cl. .......................... 340/365 R; 340/365 C; 340/365 S; 340/365 P; 434/112; 434/229
[58] Field of Search ............ 340/365 R, 365 S, 365 P, 340/365 L, 365 C; 178/101, 110; 434/229, 231, 233, 227, 112, 117; 400/472, 477, 479

[56] References Cited

U.S. PATENT DOCUMENTS

| | | | |
|---|---|---|---|
| 3,022,878 | 2/1962 | Seibel et al. | 340/365 R |
| 3,166,856 | 1/1965 | Uttal | 340/365 R |
| 3,428,747 | 2/1969 | Alferieff | 178/101 |
| 4,074,444 | 2/1978 | Laenger et al. | 340/365 R |

OTHER PUBLICATIONS

C/R/I Final Report–"Study of Man–Machine Communications Systems for the Handicapped", Kafafian, vol. III-VII, 1971.

Interim Report–"Study of Man–Machine Communications Systems for the Handicapped", Aug. 1968.

*Primary Examiner*—James J. Groody
*Attorney, Agent, or Firm*—D. M. Duft

[57] ABSTRACT

A man-machine interface is disclosed for translating discrete hand positions into electrical signals representing alpha-numeric characters. The interface comprises a glove having sensors positioned with respect to the hand for detecting the flex of finger joints and sensors for detecting the contact between various portions of the hand. Additional sensors detect the movement of the hand with respect to a gravitational vector and a horizontal plane of reference. Further additional sensors detect the twisting and flexing of the wrist. The additional sensors are associated with prescribed mode signals which determine whether subsequently formed or priorly formed character specifying hand positions are to be entered for transmission. The alpha-numeric characters associated with the formed character specifying hand positions are transmitted only when the appropriate mode signal results. The forming and moving of the hand actuates various combinations of sensors so that electrical signals representing the specified characters are generated and transmitted.

19 Claims, 17 Drawing Figures

FIG. 7

| CHAR OUTPUT | THUMB TO SENSOR: | TOUCH SENSORS | | KNUCKLE BEND SENSORS | | | | TILT SENSORS | | MODE SENS F/F |
|---|---|---|---|---|---|---|---|---|---|---|
| | | A' TO B' | C' TO D' | KBS-1 | KBS-2 | KBS-3 | KBS-4 | TS-1 | TS-2 | MODE |
| 0 | - | X | X | X | X | 1 | X | X | X | 1 |
| 1 | IJSZ1 | X | X | X | X | 0 | 1 | X | X | 1 |
| 2 | RUV2 | 0 | X | X | X | X | 1 | X | X | 1 |
| 3 | - | X | X | X | X | 0 | X | X | X | 1 |
| 4 | B4 | X | X | X | X | X | 1 | X | X | 1 |
| 5 | - | X | X | X | X | 0 | 0 | X | X | 1 |
| 6 | W6 | X | X | X | X | X | X | X | X | 1 |
| 7 | 7 | X | X | X | X | X | X | X | X | 1 |
| 8 | D8 | X | X | X | X | X | X | X | X | 1 |
| 9 | 09 | X | X | X | X | X | X | X | X | 1 |
| A | A | X | X | X | X | X | X | X | X | 0 |
| B | B4 | X | X | 0 | X | 1 | 1 | X | X | 0 |
| C | - | X | X | X | X | X | X | X | X | 0 |
| D | D8 | X | X | X | X | 1 | 1 | X | X | 0 |
| E | - | X | X | 1 | X | 1 | X | X | X | 0 |
| F | F | X | X | X | X | X | X | X | X | 0 |
| G | GT | X | X | X | X | 0 | 0 | X | X | 0 |
| H | HNX | X | X | X | 0 | X | X | X | X | 0 |
| I | IJSZ1 | X | X | X | X | X | X | 1 | X | 0 |
| J | IJSZ1 | X | X | X | X | X | 0 | 0 | X | 0 |
| K | KP | X | X | X | X | X | X | X | 1 | 0 |
| L | - | X | X | X | X | X | X | X | 1 | 0 |
| M | M | X | X | X | X | X | X | X | X | 0 |
| N | HNX | X | X | X | 1 | X | X | X | X | 0 |
| O | 09 | X | X | X | X | X | X | X | 0 | 0 |
| P | KP | X | X | X | X | X | X | X | 0 | 0 |
| Q | - | X | X | X | X | 0 | X | X | 0 | 0 |
| R | RUV2 | 1 | X | X | X | X | 1 | X | X | 0 |
| S | IJSZ1 | X | X | X | X | 1 | 1 | X | X | 0 |
| T | GT | 0 | X | X | X | 1 | X | X | X | 0 |
| U | RUV2 | 0 | 1 | X | X | X | X | X | X | 0 |
| V | RUV2 | 0 | 0 | X | X | X | X | X | X | 0 |
| W | W6 | X | X | X | X | 0 | X | X | X | 0 |
| X | HNX | X | X | X | 0 | X | X | X | X | 0 |
| Y | - | X | X | X | X | 1 | 1 | 0 | X | 0 |
| Z | IJSZ1 | X | X | X | X | X | 0 | 1 | X | 0 |

FIG. 16

| CHAR OUTPUT | TOUCH SENSORS THUMB TO SENSOR: | KNUC. BEND SENS KBS | TILT SENSORS TS-1 | TILT SENSORS TS-2 | CHAR. OUTPUT | TOUCH SENSORS THUMB TO SENSOR: | KNUC. BEND SENS KBS | TILT SENSORS TS-1 | TILT SENSORS TS-2 |
|---|---|---|---|---|---|---|---|---|---|
| 0 | 16 | 0 | 0 | 1 | Y | 9 | 1 | 1 | 0 |
| 1 | 1 | 0 | 0 | 1 | Z | 10 | 1 | 1 | 0 |
| 2 | 2 | 0 | 0 | 1 | [ | 11 | 1 | 1 | 0 |
| 3 | 3 | 0 | 0 | 1 | \ | 12 | 1 | 1 | 0 |
| 4 | 7 | 0 | 0 | 1 | ] | 13 | 1 | 1 | 0 |
| 5 | 8 | 0 | 0 | 1 | ^ | 14 | 1 | 1 | 0 |
| 6 | 9 | 0 | 0 | 1 | — | 15 | 1 | 1 | 0 |
| 7 | 13 | 0 | 0 | 1 | ` | 16 | 1 | 1 | 0 |
| 8 | 14 | 0 | 0 | 1 | a | 1 | 0 | 0 | 0 |
| 9 | 15 | 0 | 0 | 1 | b | 2 | 0 | 0 | 0 |
| : | 4 | 0 | 0 | 1 | c | 3 | 0 | 0 | 0 |
| ; | 5 | 0 | 0 | 1 | d | 4 | 0 | 0 | 0 |
| < | 6 | 0 | 0 | 1 | e | 5 | 0 | 0 | 0 |
| = | 10 | 0 | 0 | 1 | f | 6 | 0 | 0 | 0 |
| > | 11 | 0 | 0 | 1 | g | 7 | 0 | 0 | 0 |
| ? | 12 | 0 | 0 | 1 | h | 8 | 0 | 0 | 0 |
| A | 1 | 1 | 0 | 0 | i | 9 | 0 | 0 | 0 |
| B | 2 | 1 | 0 | 0 | j | 10 | 0 | 0 | 0 |
| C | 3 | 1 | 0 | 0 | k | 11 | 0 | 0 | 0 |
| D | 4 | 1 | 0 | 0 | l | 12 | 0 | 0 | 0 |
| E | 5 | 1 | 0 | 0 | m | 13 | 0 | 0 | 0 |
| F | 6 | 1 | 0 | 0 | n | 14 | 0 | 0 | 0 |
| G | 7 | 1 | 0 | 0 | o | 15 | 0 | 0 | 0 |
| H | 8 | 1 | 0 | 0 | p | 16 | 0 | 0 | 0 |
| I | 9 | 1 | 0 | 0 | q | 1 | 0 | 1 | 0 |
| J | 10 | 1 | 0 | 0 | r | 2 | 0 | 1 | 0 |
| K | 11 | 1 | 0 | 0 | s | 3 | 0 | 1 | 0 |
| L | 12 | 1 | 0 | 0 | t | 4 | 0 | 1 | 0 |
| M | 13 | 1 | 0 | 0 | u | 5 | 0 | 1 | 0 |
| N | 14 | 1 | 0 | 0 | v | 6 | 0 | 1 | 0 |
| O | 15 | 1 | 0 | 0 | w | 7 | 0 | 1 | 0 |
| P | 16 | 1 | 0 | 0 | x | 8 | 0 | 1 | 0 |
| Q | 1 | 1 | 1 | 0 | y | 9 | 0 | 1 | 0 |
| R | 2 | 1 | 1 | 0 | z | 10 | 0 | 1 | 0 |
| S | 3 | 1 | 1 | 0 | { | 11 | 0 | 1 | 0 |
| T | 4 | 1 | 1 | 0 | \| | 12 | 0 | 1 | 0 |
| U | 5 | 1 | 1 | 0 | } | 13 | 0 | 1 | 0 |
| V | 6 | 1 | 1 | 0 | ~ | 14 | 0 | 1 | 0 |
| W | 7 | 1 | 1 | 0 | SPACE | 17 | X | X | X |
| X | 8 | 1 | 1 | 0 | DELETE | 18 | X | X | X |

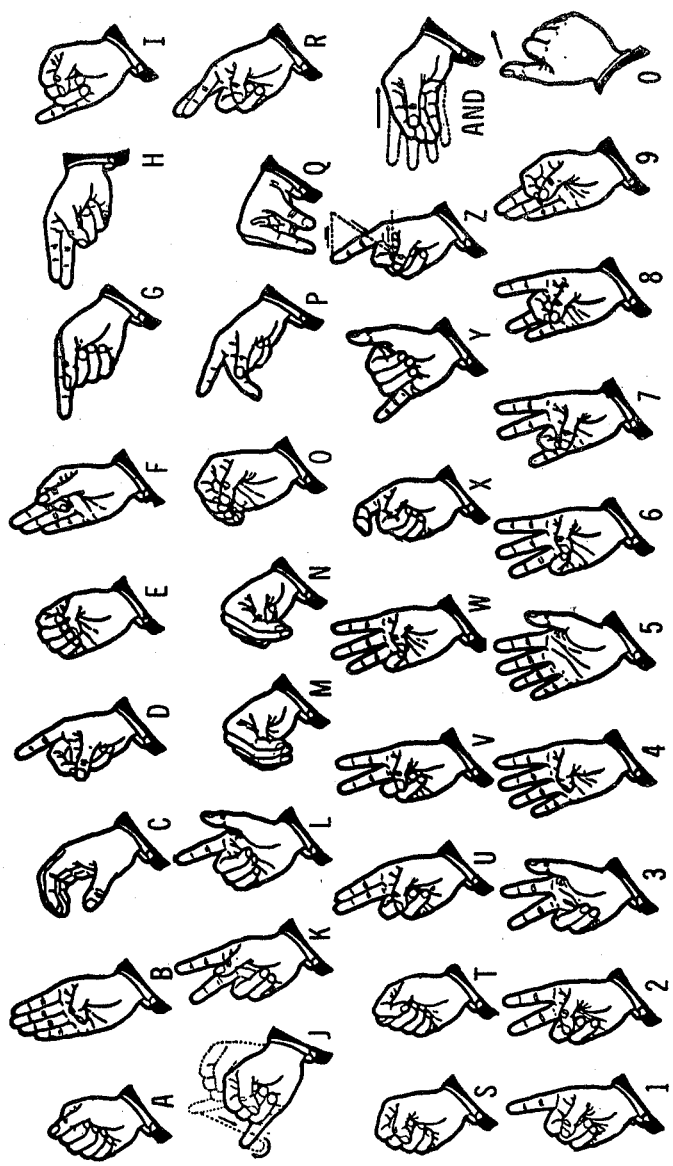
SINGLE HAND MANUAL ALPHABET  FIG. 17

DIGITAL DATA ENTRY GLOVE INTERFACE DEVICE

TECHNICAL FIELD

This invention relates to a man-machine interface and in particular to an interface that permits a user to input data, including alphanumeric and control information, with increased ease and efficiency to electric typewriters, computers, terminals and other types of data utilization devices. This invention further relates to a man-machine interface for translating discrete hand positions representing data characters into corresponding electrical signals. More specifically, the invention relates to a glove equipped with sensors for detecting character specifying hand movements. The forming of the hand and fingers into the different character specifying positions activates various combinations of sensors so that electrical signals representing the specified characters are generated.

BACKGROUND OF THE INVENTION

Man-machine interfaces of varying degrees of complexity are commonly used to input data to machines. These interfaces cover the spectrum from the relatively simple to complex keyboards used to input data to electric typewriters and computers. Although the currently available interface devices are adequate for their intended purpose, they are less than ideal from both a human factors as well as from an economic standpoint.

For example, the currently available typewriter and computer terminal keyboards are large, bulky, and complex. Also, due to their complexity, they are expensive and often malfunction. Another disadvantage is that they require an operator using them to sit in a fixed position proximate the keyboard.

It is known to use special purpose data input devices in place of keyboards. U.S. Pat. No. 3,022,878 to R. Seibel, of Feb. 27, 1962 discloses a data input device comprising a glove-like casing 1 having a plurality of switches 4 adapted to receive the distal phalanges of a user's hand inserted into the glove. The switches 4 are of the multiposition type and they are selectively and combinationally set by the user's phalanges to various character representing positions in order to transmit data to an associated machine.

The Seibel et al device may, perhaps, overcome some of the disadvantages of the conventional keyboards. However, it does not represent a universal solution since it is bulky, complex, and is designed for special purpose applications such as, for example, airplane cockpits.

SUMMARY OF THE INVENTION

The disadvantages of the prior art keyboards and other data entry devices are overcome by the present invention which comprises a data entry glove equipped with sensors that permit a user wearing the glove to generate data signals by moving his or her hand to form different character specifying positions. The sensors respond to the different hand positions and movements including the position of the metacarpus relative to the gravitational vector, the motion of the metacarpus relative to an initial frame of reference, and positions of the phalanges including flexing of the phalanx joints.

The data entry glove embodying the invention includes a first group of sensors fixed to the back of the metacarpus portion of the glove to identify the planar position of the metacarpus relative to the gravitational vector. It further includes a second group of sensors on the back metacarpus portion of the glove to detect motion relative to an initial frame of reference. A third group of sensors are attached to the phalanx portions of the glove to detect the flexing of selected phalanx joints. A fourth group of sensors are affixed to selected phalanx areas of the glove. The sensors of this group are contact sensitive and their selective contact with one other sensor as the hand assumes various character specifying positions is part of the process by means of which the groups of sensors, working in combination, detect hand positions and movements and, in turn, transmit corresponding character specifying signals to a data utilization device.

A user wearing the data entry glove device of the present invention may generate information, including alpha-numeric data and control characters, by moving his or her hand to form various positions successively in sequence. Each such position is unique to a different character or other data that can be transmitted by the glove to a data receiving device.

One embodiment of the invention comprises a glove equipped with sensors and associated electronic logic which is designed for use by the deaf or hearing impaired who are skilled in the use of a sign language termed Single Hand Manual Alphabet for the American Deaf. This permits a deaf or hearing impaired user wearing the data entry glove to input data to a receiving device by forming his or her hand into the character positions defined by the Single Hand Manual Alphabet. This embodiment of the invention is advantageous in that it permits a user who is familiar with this hand language, but who has no typing or other keyboard skills, to input information to a machine and, at the same time, to communicate visually with another hearing impaired person.

A second embodiment of the invention is similar to the first except that the sensors are positioned to respond to a set of hand signals that is more efficient for the generation of data for electric typewriters and data processing equipment.

Both embodiments of the invention are an advance in the art in that they provide a man-machine interface in the form of a data entry glove that is easy to use and does not require an operator to sit at a keyboard proximate the controlled machine to which data is being inputted. Also, the data entry glove embodying the present invention is not bulky, is of lesser complexity, and, therefore of enhanced reliability with respect to the prior art devices.

BRIEF DESCRIPTION OF THE DRAWINGS

This invention may be understood by reading the following detailed description with reference to the accompanying drawings wherein:

FIGS. 1-11 disclose an embodiment of the invention adapted for use with the Single Hand Manual Alphabet of the American Deaf.

FIGS. 12-16 disclose an embodiment of the invention adapted for use with an arbitrary hand alphabet.

FIG. 17 discloses the Single Hand Manual Alphabet for the American Deaf.

DETAILED DESCRIPTION

Figure 1:
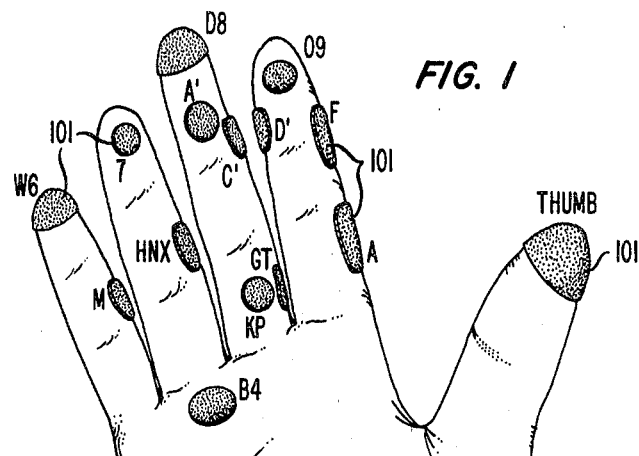
Figure 2:
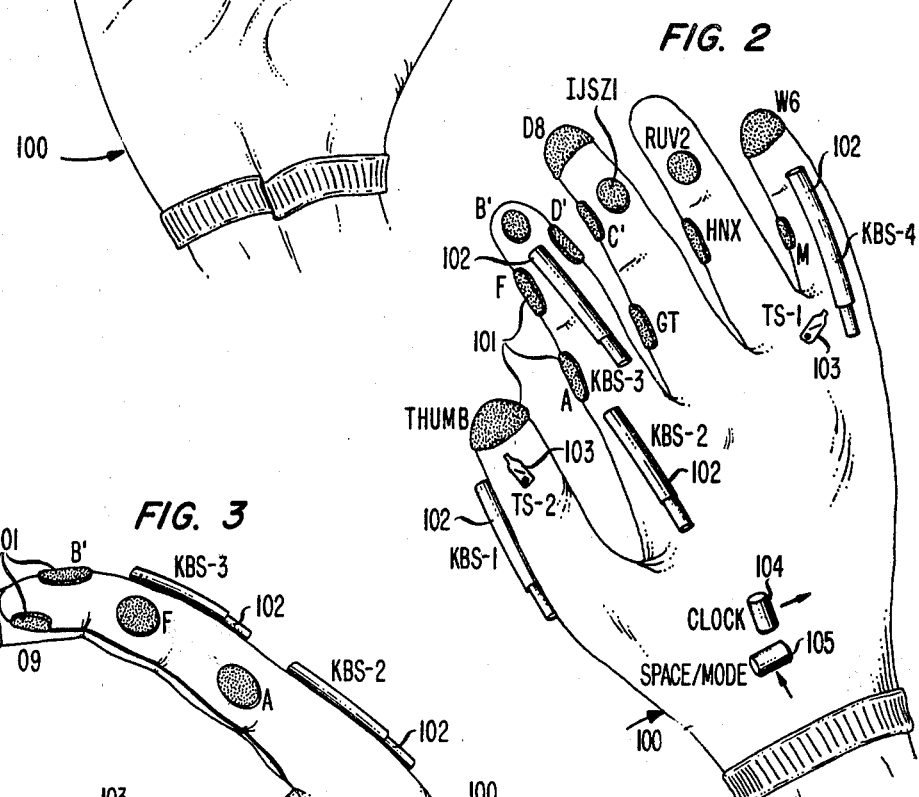
Figure 3:
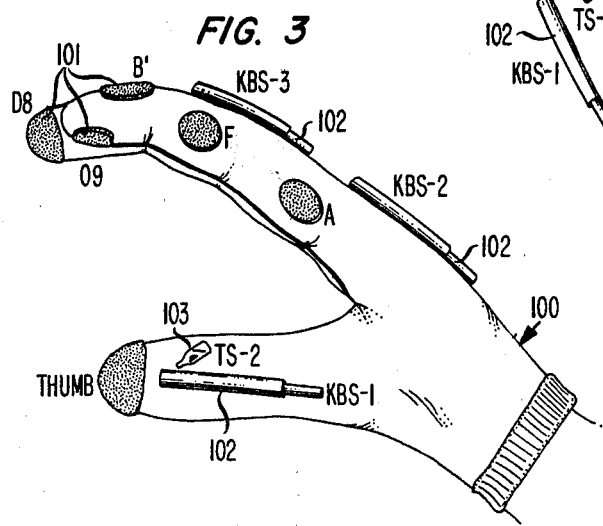

FIGS. 1, 2, and 3 disclose a data entry glove 100 equipped with the sensors required for use with the Single Hand Manual Alphabet. The glove's output results from the state of various types of sensors that are parts of the glove. These sensors provide information about (1) whether or not certain joints of the hand are bent; (2) whether or not certain parts of the hand, fingers, and thumb are touching each other; (3) the positions of various portions of the hand relative to the gravitational vector; (4) and motion of the hand relative to an inertial frame of reference. Hand gestures made by a user wearing the glove activate combinations of sensors to produce like combinations of true (1) bits.

A first type of sensors on FIG. 1 is termed "touch/proximity" sensors, and have the reference designation 101. These are shown as shaded areas on FIGS. 1, 2, and 3 and are generally of circular, semicircular, or oblong configuaration. These sensors produce an output indicating whether certain fingers are touching or when the tip of the thumb is touching the hand or any of the fingers. With the exception of two pairs of the touch sensors, all sensors 101 are sensitive only to contact with a THUMB sensor. The exceptions are sensors A', B', C', and D'. Sensor A' is sensitive to contact with Sensor B'; Sensor C' is sensitive to contact with Sensor D'.

When a user wearing the glove makes hand gestures symbolizing letters of the Single Hand Manual Alphabet, (FIG. 17) appropriate touch sensors make contact and generate an output signal. The touch sensors 101 are also designated by the characters to which they are sensitive. Certain sensors 101 have only a single character designation (7, A, F, M). These generate the corresponding character when in contact with the THUMB sensor. Others have a multiple character designation (B4, KP, IJSZ1, etc. ) and are associated with all of the corresponding characters.

These touch/proximity sensors 101 can be conductive pads, Hall effect sensors, membrane switches, or capacitive switches. In the subject embodiments, the touch/proximity sensors 101 are silver-filled conductive rubber pads that make electrical contact when they touch each other. Associated circuitry is connected to these pads and treats them as switch contacts. Since these pads are sensitive to touch, they will be called touch sensors for the rest of this description.

A second type of sensors on FIGS. 1, 2, and 3 are the sensors 102 which are termed "knuckle-bend sensors". These sensors are also designated KBS1, KBS2, KBS3, and KBS4. Each knuckle-bend sensor 102 spans a joint of the hand wearing the data entry glove. Each sensor 102 flexes with the joint it spans and generates a true signal when its joint is flexed.

Figure 4:
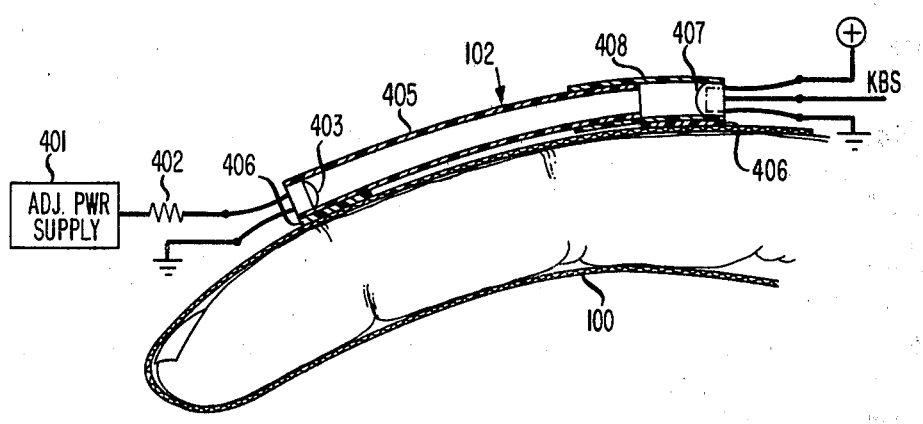
Figure 5:
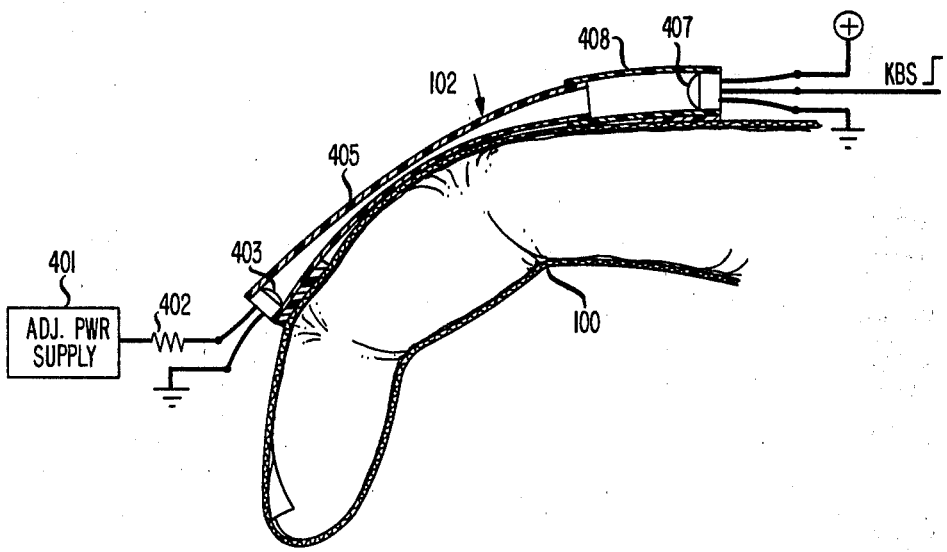

A knuckle-bend sensor may be any device that reacts to the stress produced on the data entry glove by flexing the corresponding joint. Such a device might use optical, Hall effect, conductive elastomeric, or strain gage sensors. The optical sensor shown in FIGS. 4 and 5 is used in the given embodiments. In FIGS. 4 and 5 the sensor may be seen in the extended (FIG. 4) and flexed (FIG. 5) positions.

FIG. 4 illustrates in detail the construction of a knuckle-bend sensor 102. Infrared emitting diode 403 faces opto-schmidt detector 407 through a two piece tube comprising tube 405 and large r diameter tube 408. The walls of this assembly (405, 408) are opaque to exclude ambient radiation, and each component tube is affixed at its end to the surface of the glove (100) by means of cement 406. Since the tube ends are fixed, tube 405 slides within tube 408 as the sensor is flexed.

Current from an adjustable power supply 401 to infrared emitting diode 403 (limited by resistor 402) causes diode 403 to emit infrared radiation that activates opto-schmidt detector 407. Detector (407) includes a threshold detector that causes the state of its signal lead KBS to change abruptly at a certain level of radiation as intensity increases, and at a slightly lower level as intensity decreases.

Diode 403 is so chosen and the sensor is so constructed that radiation intensity within the sensor is above the high threshold level when the sensor is not flexed (FIG. 4). When the sensor is flexed by the knuckle that it spans (FIG. 5), tube 405 bends and partially flattens. This restricts the path that the radiation takes from diode 403 to detector 407. When tube 405 is restricted, radiation intensity reaching detector 407 is below the low threshold level. This causes the signal from 407 on lead KBS to change state to a true condition to indicate that the associated knuckle is bent.

A third type of sensors on FIGS. 1, 2, and 3 is sensors 103 which are termed "tilt sensors". These are also designated as sensors TS-1 and TS-2. Any conventional tilt sensor may be used for this purpose. The basic requirement is that the electrical output of the sensor change state as the sensor is tilted through the horizontal plane.

Each tilt sensor 103 on the given embodiments is an ordinary mercury switch comprising a sealed tube with two electrodes in one end and a pool of mercury which flows as the tube is tilted. When the end of the tube with the electrodes is held lower than the other end, the pool of mercury contacts the two electrodes and closes the circuit between them. When the end of the tube with the electrodes is held higher than the other end, the pool of mercury resets in the empty end of the tube. This leaves an open circuit between the electrodes. For example, sensor TS-1 is placed so that the electrodes are nearest the wrist. Therefore when TS-1 is held above the level of the wrist, the mercury flows towards the wrist and makes contact between the electrodes.

A fourth type of sensors on FIGS. 1, 2, and 3 are the inertial sensors 104 and 105 which are also designated CLOCK and SPACE/MODE on FIG. 1. These are common inertial switches known to the art. The type used in the present invention incorporates a hold plated ferrous ball, a magnet, and two electrodes at the end of the sensor opposite the magnet. The ball is normally held to the magnet. Under sufficient acceleration opposite the direction of the force of the magnet, the inertia of the ball makes it leave the magnet and short together the electrodes. The direction of sensitivity or electrode contact is indicated by arrows on FIG. 1. Since sensors 104 and 105 are directional, and since they are mounted at right angles to each other on the glove, two distinct motions of the hand are detected. The CLOCK sensor detects a twisting of the forearm (as when turning a screwdriver). The SPACE/MODE sensor detects a flexing of the wrist (as when knocking on a surface).

Hand positions specifying certain letters or numbers activate unique combinations of the touch and tilt sensors. The letters K and P of the Manual Alphabet, for example, require similar positions of the hand. The THUMB sensor contacts sensor KP for both of the K and P characters. However the gesture for K calls for the thumb to be up (activating tilt sensor TS-2) and the gesture for P calls for the thumb to be down (tilt sensor TS-2 deactivated). Reflecting such distinctions, the sensor output lines on this glove exhibit the bit patterns shown in FIG. 7. The bit patterns of FIG. 7 are unique to each character and associated circuitry can decode the patterns for use in logic state machines.

Figure 6:
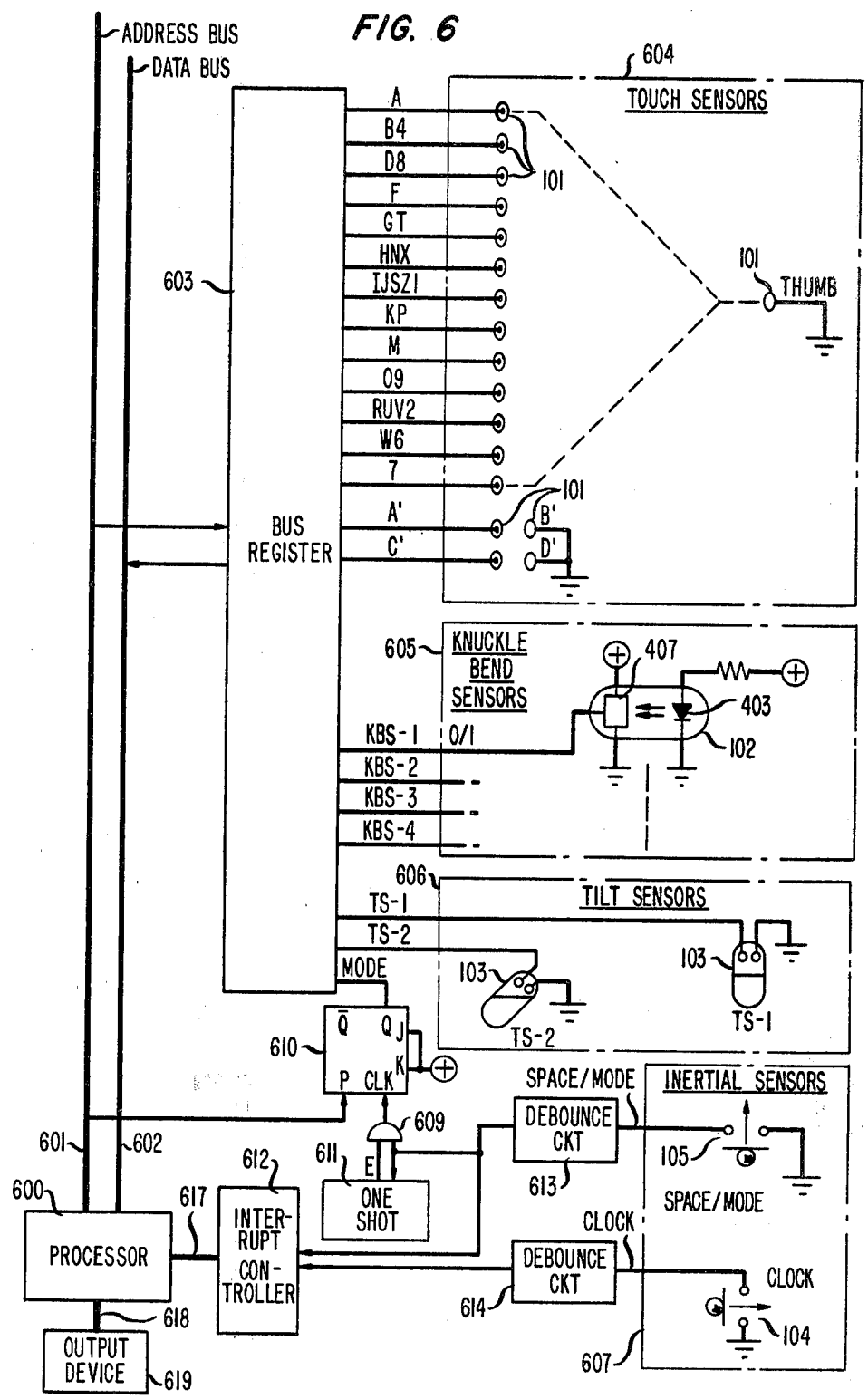

FIG. 6 discloses the circuitry used to transform output signals from the Single Hand Manual Alphabet Data Entry Glove 100 into the American Standard Code for Information Interchange (ASCII). By means of the example to be described, the subject data entry glove can be connected by the circuitry of FIG. 6 to any logic state machine that reads ASCII.

Rectangles 604, 605, 606, snf 607 on FIG. 6 encompass the glove sensors. Touch sensors 101 are in rectangle 604, knuckle-bend sensors 102 (KBS-) are in rectangle 605, tilt sensors 103 (TS-1 and TS-2) are in rectangle 606; the SPACE/MODE sensor 105, and the CLOCK sensor 104 are in rectangle 607.

The signals from the sensors are applied to register 603. The input line of register 603 contains pull-up resistors that render their inputs high when the corresponding sensors are not activated. Thus, when the grounded THUMB sensor touches the F sensor, the F line into register 603 is drawn low. When the user's thumb is up (tilt sensor TS-2 held above the wrist), tilt sensor TS-2 is activated and line TS-2 is drawn low. Each knuckle-bend sensor 102 applies a true, a high, to its corresponding register input when the sensor is flexed.

Another signal that enters register 603 is the Mode signal from flip-flop 610. This advises the processor whether the generated signals represent letters or numbers. When a user wearing the data entry glove makes a knocking motion, SPACE/MODE sensor 105 sends a signal to debounce (and inverter) circuit 613 which, in turn, sends a high signal to AND gate 609. As subsequently described, one such signal is interpreted as a space, two in quick succession are interpreted as a change of mode (such as from letters to numbers). AND gate 609 and One Shot circuit 611 use adjacent SPACE/MODE signals from debounce circuit 613 to generate a signal that changes the state of JK flip-flop 610. This causes a change of the Mode signal on its $\mp$Q" output. One Shot 611 is triggered by the trailing edge of the first SPACE/MODE signal. When so triggered, One Shot 611 partially enables AND gate 609 over path "E". The gate remains partially enabled by circuit 611 for the period which is adjustable to allow just enough time for the operator to activate SPACE/MODE sensor 105 twice. When a SPACE/MODE signal appears at the input of AND gate 609 while it is enabled by One Shot 611, the resulting signal from gate 609 changes the state of flip-flop 610. This changes the Mode signal applied to register 603. Thus, the second of each pair of SPACE/MODE signals is made into a change Mode signal.

Flip-flop 610 is of the JK type and switches to a different state upon each receipt of a signal on its CLK input. The flip-flop is initialized to its preset (P) state by the processor when the system is first turned on. This is done as the processor applies to the appropriate signal to the preset input of the flip-flop. The preset state is defined at the "letters mode" state in which the Q output of the flip-flop is high (not at ground). Thus, when the system is first turned on, flip-flop 610 and the system of FIG. 6 are in the letters mode in which the hand signals generated by a user are translated into the appropriate alphabetical characters in accordance with the chart of FIG. 7. The next change of state of the flip-flop in response to a SPACE/MODE interrupt from sensor 104 switches the flip-flop to the numbers mode in which the circuit of FIG. 6 outputs numbers in the response to the hand signals generated by the user.

As shown on FIG. 7 in the right-hand column, the Q output of flip-flop 610 is high during its letters mode. Conversely, the Q output is at ground potential when the flip-flop is in the numbers mode. This represents a binary true or a "1" condition in the present disclosure. The Q signal is applied to the register and scanned by the processor which uses this information to identify those hand signals that may represent either an alphabetical character or a number. Each SPACE/MODE signl (from SPACE/MODE sensor 105 via debounce circuit 613) is also applied to processor 600 by interrupt controller 612 via interrupt bus 617. The action taken by 600 in response to these interrupts is subsequently explained in the flowchart description on FIG. 8 et seq.

An interrupt signal can also be sent to processor 600 from CLOCK sensor 104 via debounce circuit 614 and interrupt controller 612. Debounce circuit 614 provides a true CLOCK signal to interrupt controller 612 in response to a signal from CLOCK sensor 104. When the processor 600 receives a CLOCK signal interrupt, the processor briefly terminates its scanning of register 603 and begins a process in which it determines the character represented by the last hand position whose information was inputted to register 603 and scanned by the processor. It converts this information to ASCII and outputs it over path 618 to output device 619.

The precessor normally scans the register every 10 milliseconds and stores the scan results in its memory.

Signals from processor 600 are applied over address bus 601 and data bus 602 to scan the register 603 and cause it to send data to processor 600. Since the hand movements associated with the generation of a clock signal may cause other sensors to generate transient signals representing illegal or unwanted characters, the processor does not output the information for the last few characters scanned. Instead, it reads out that location of its memory that contains the information for the character that was scanned just before the user's hand moved to generate the CLOCK interrupt signal. This prevents the processor from outputting invalid data.

FIGS. 8-11 disclose how the processor generates ASCII character information in response to the receipt of the previously described sensor data. FIGS. 8-11 disclose the order in which the tests are made by the processor as well as the order in which the ASCII data is written on ASCII bus 618.

Figure 8:
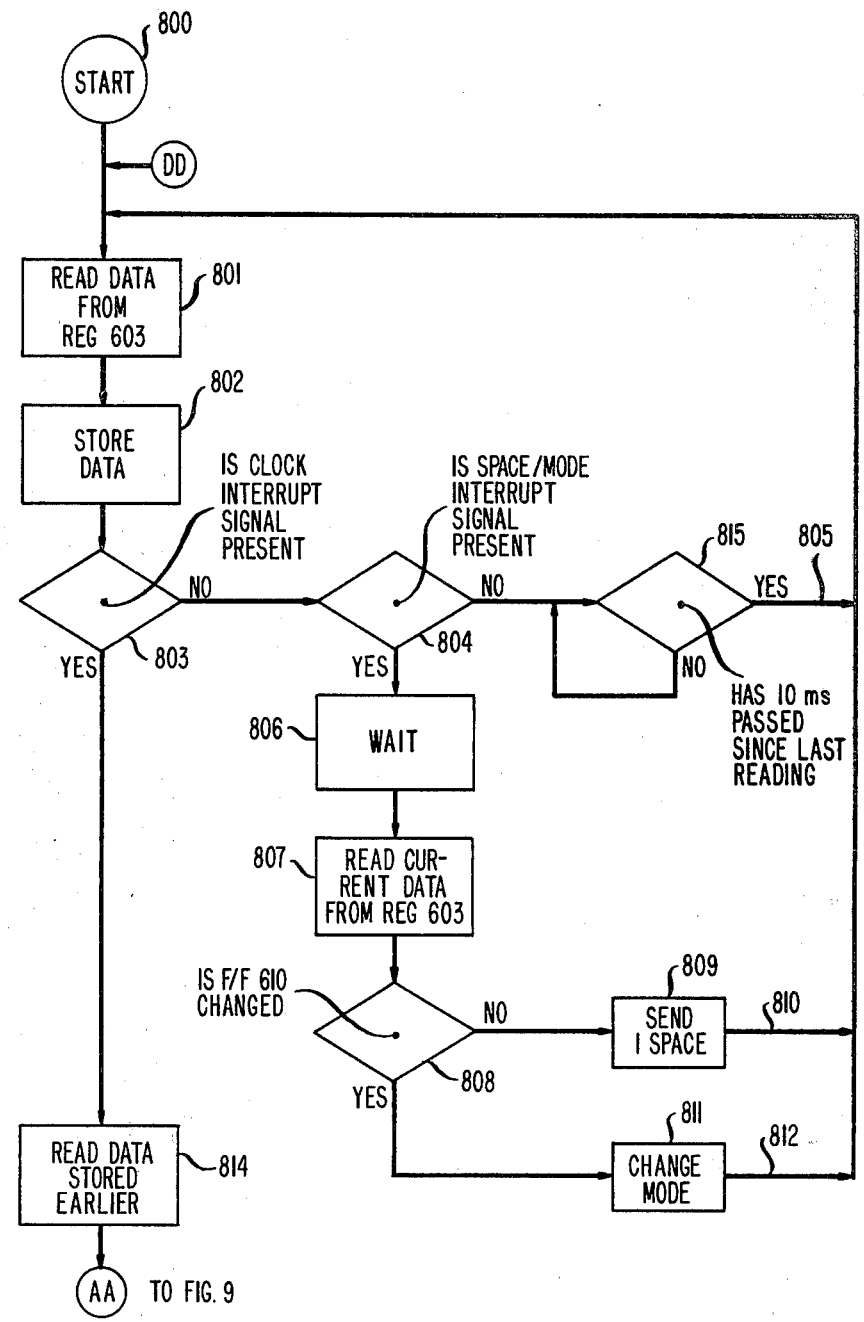
Figure 9:
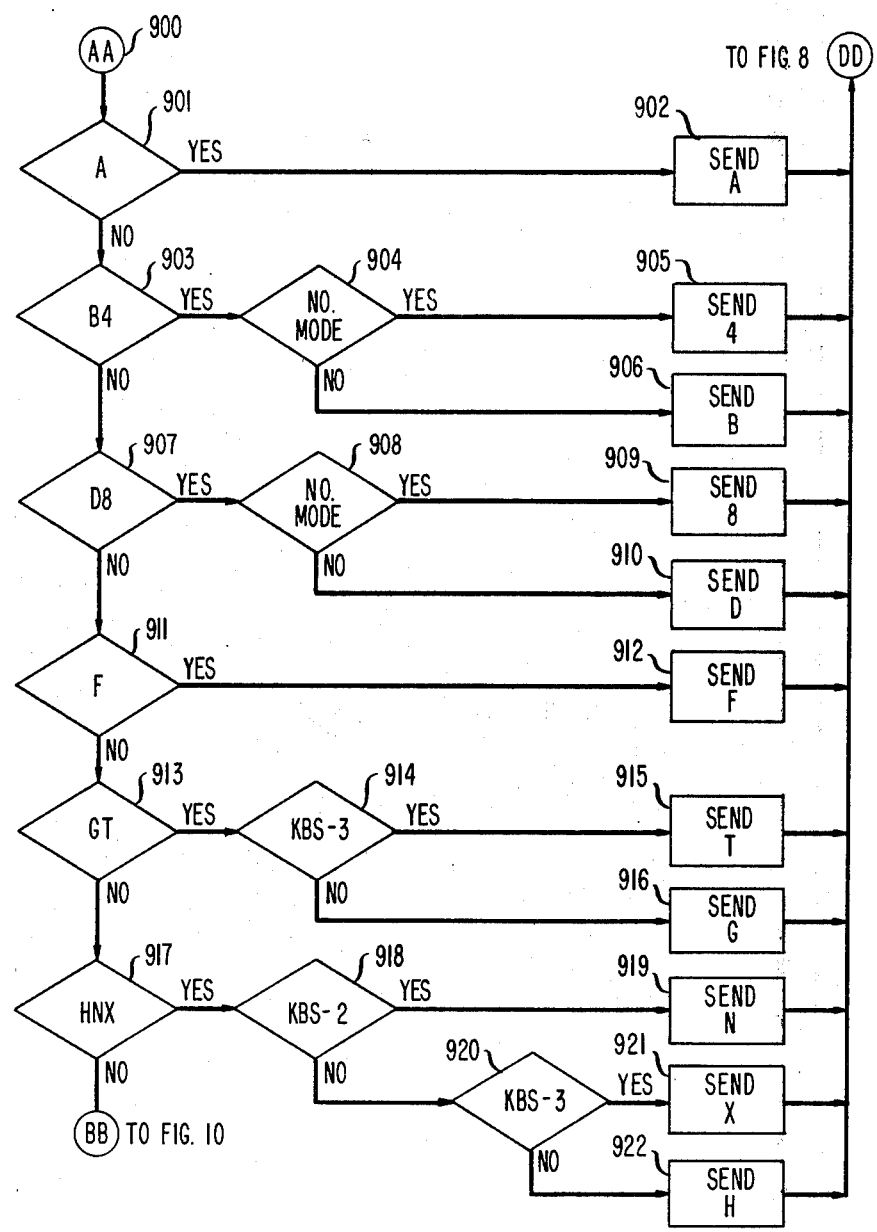
Figure 10:
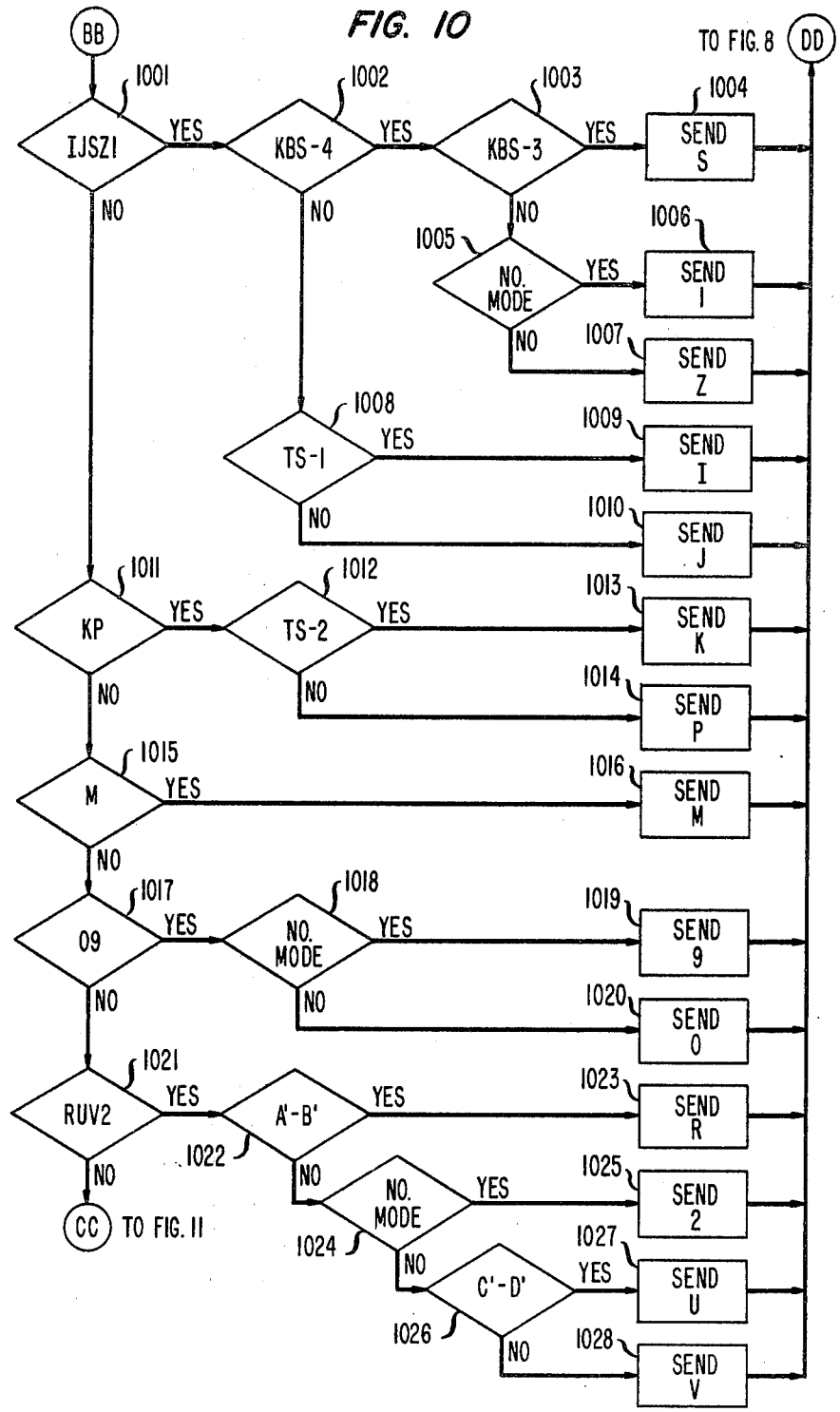
Figure 11:
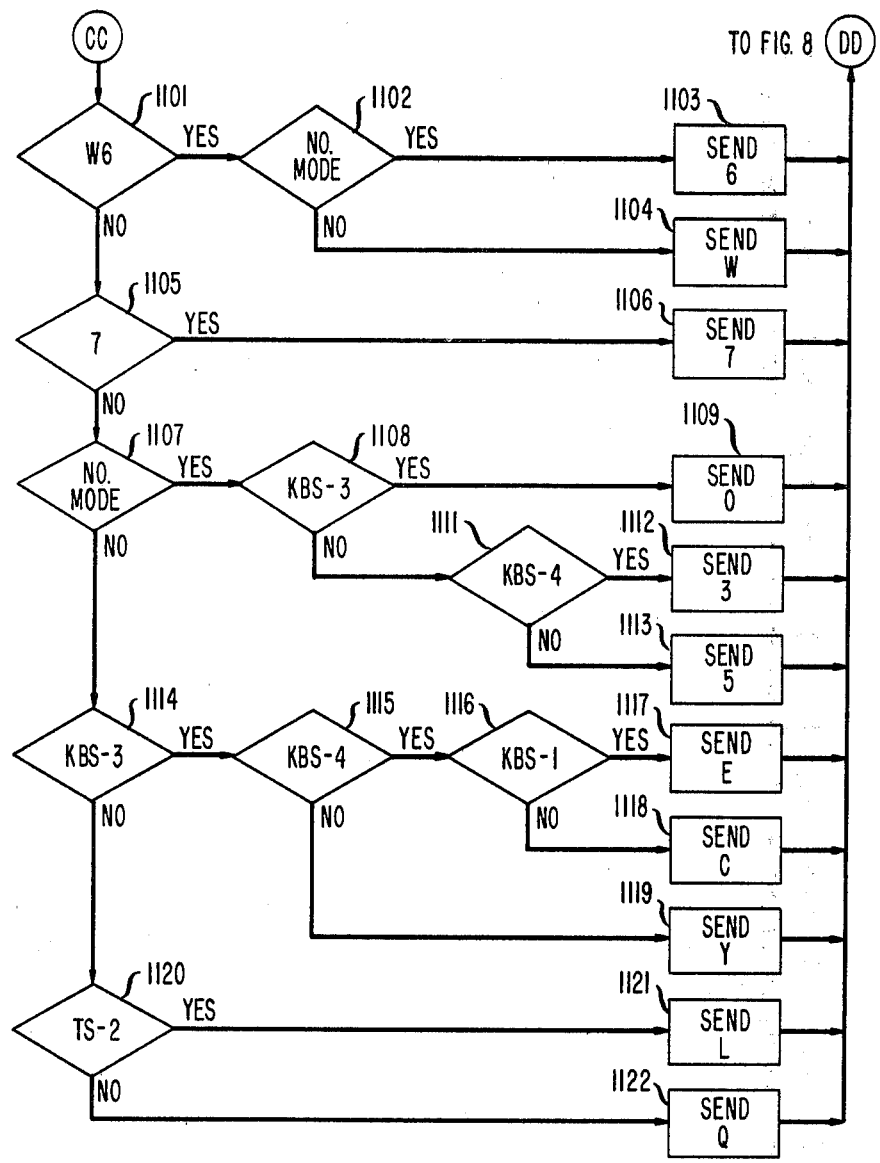

The process begins at the start terminal 800 of FIG. 8. Beginning at this point, processor 600 scans the register data bus 602 every 10 milliseconds and stores the scan results in its memory. This is accomplished by means of the "read register loop" comprising elements 801-805 and 815. When the "read register loop" is interrupted at 803 by a CLOCK interrupt, processor 600 proceeds to read out to element 619 ASCII information derived from the data earlier received from register 603 and stored in the processor memory. When the "read register loop" process is interrupted at 804 by a SPACE/MODE interrupt (804), the processor (600) is programmed to wait (806) for a period exceeding that of One Shot 611. After the wait interval (806) has passed, the processor reads (807) the data currently stored in register 603 to determine whether the signal from sensor 105 represents a SPACE or MODE interrupt. In element 808, the processor looks at the MODE signal applied by the Q output of flip-flop 610 to register 603 to determine whether the flip-flop has changed state. If it has not changed, this means that only one signal was generated by sensor 105 and that this represents a space character. This being the case, the processor outputs (809) an ASCII space character to output device 619. From element 809, the processor's operation goes back and reads data from register 603 as shown in element 801.

On the other hand, if the processor in element 808 determines that flip-flop 610 has changed state, it recognizes that two signals were generated by sensor 105 and that these two signals represent a "change of mode" interrupt. Accordingly, processor (811) changes its internal mode of operation, reverts back to the beginning of the flowchart in element 801 and prepares to read the subsequent characters generated by the user. In other words, if the processor was previously set to read letters, it now changes its mode to read numbers; if it was set to read numbers, it now changes its mode to read letters.

As already mentioned, the processor functions to generate an output character in ASCII and apply it to output device 619 once for each clock interrupt signal it receives as shown by elements 803 and 814. Upon the receipt of each clock signal, the section of the processor memory is read (814) that contains the last valid data read from register 603 and representing the user's stable hand position at that time. This data is translated by the processor to ASCII and applied to output device 619. The algorithm used by the processor to evaluate this data in memory and generate the appropriate ASCII character is shown on FIGS. 9, 10, and 11. On FIG. 8 after the processor determines (element 803) that a clock signal has been received, it reads the data in memory (814) and proceeds to FIG. 9 to identify the appropriate character. If, for example, the A bit is true (901), the process shown on the flowchart goes through element 902 to send an ASCII "A" to device 619. the process is then ended and a new one begun starting with element 801.

More than one bit must be true, as shown on FIG. 7, to identify certain characters. For example, assume that no bits are found to be true until the GT bit is tested (913). The character sent depends on the state of sensor KBS-3 at the time the GT sensor is activated. If the KBS-3 bit is true (914), the character "T" is sent (915), if false, "G" is sent (916).

Another type of decision remains to be described. If no bits are found to be true until the B4 bit (903), for example, the character sent depends on whether the system is in the number or letter mode (904). If the system is in number mode, a "4" is sent (905), if not a "B" is sent (906).

A more complex determination involves sensor RUV2. After it is determined that sensor RUV2 is active (1021), the decisions of elements 1022, 1024, and 1026 must be made to determine whether the current hand position specifies the character R, 2, U, or V. Another complex determination involves the sensor 1JSZI (1001) to identify the character S, 1, Z, I, or J.

All decisions in the selection process are of the types just described. By means of this process, all of the characters from A to Z and 0 to 9 can be sent.

Figure 12:
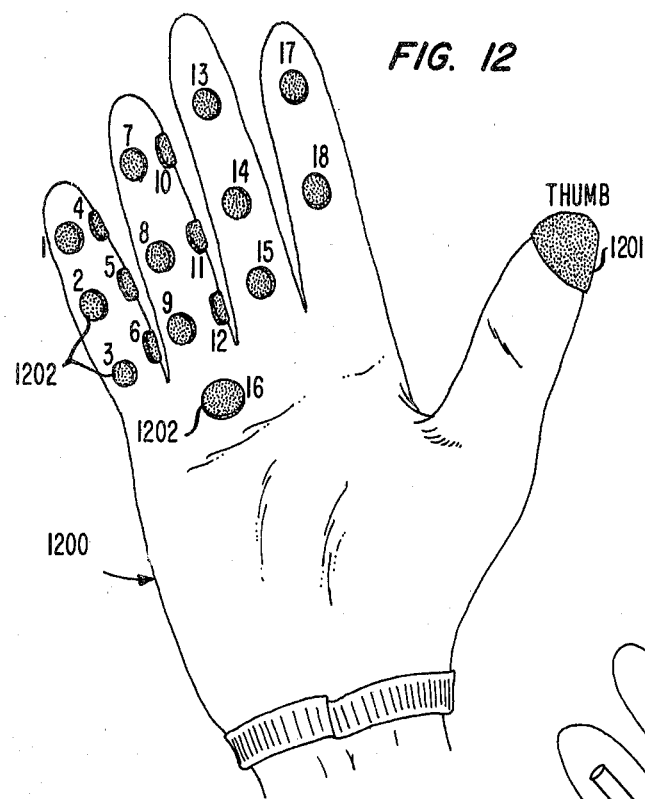
Figure 13:
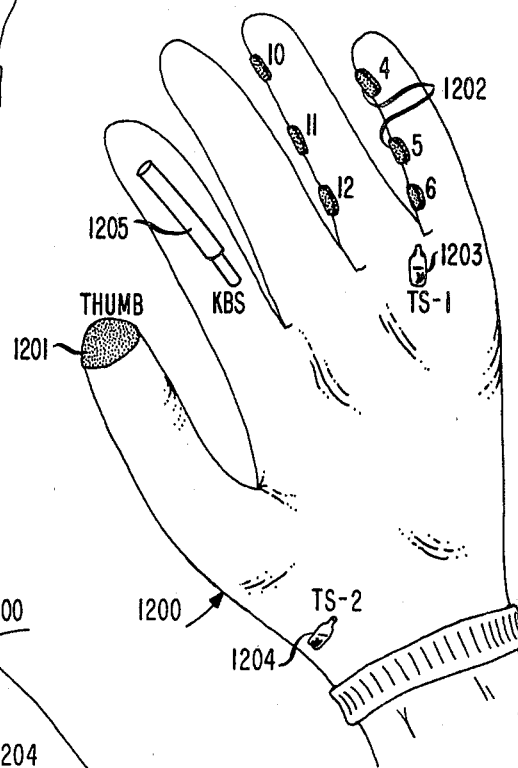
Figure 14:
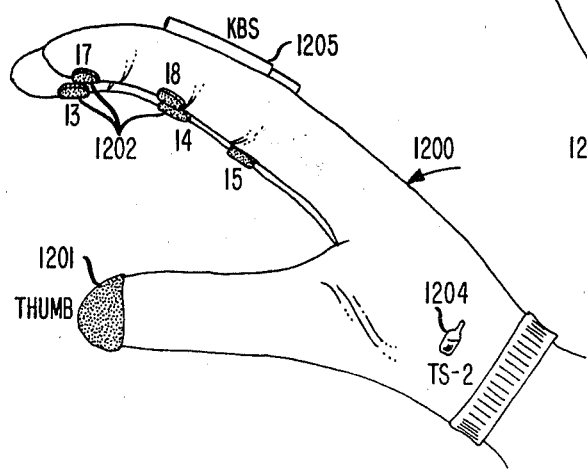

The embodiment of the invention adapted for use with business terminals is shown on FIGS. 12-16. FIGS. 12, 13, and 14 illustrate the sensors and their positions on the glove 1200 for this embodiment. As shown, it consists of a THUMB sensor 1201 and a plurality of numerically designated sensors 1202 that may be selectively contacted to the THUMB sensor 1201 one at a time. This embodiment of FIGS. 12-14 further includes tilt sensors 1203 and 1204 which are also designated as TS-1, and TS-2, respectively. This embodiment further includes a knuckle-bend sensor 1205 which is also designated KBS. The functions of these sensors are comparable to the corresponding sensors of the earlier described embodiment and therefore need not be described in further detail.

Figure 15:
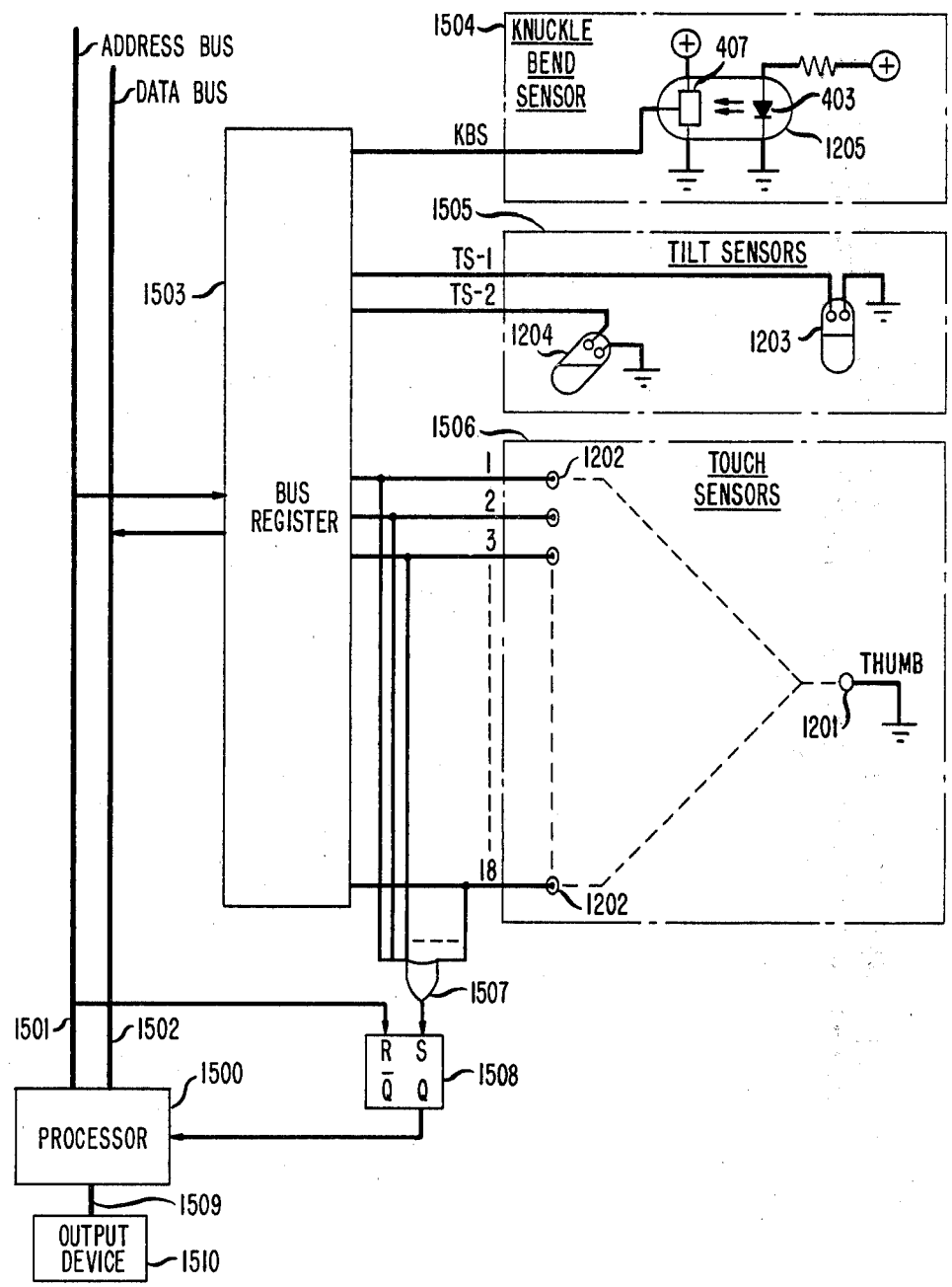

FIG. 15 discloses the circuitry used to translate the character specifying hand positions of this embodiment into the appropriate ASCII characters for transmission to output device 1510. The circuitry of FIG. 15 is similar to that of FIG. 6 and therefore need be only described briefly. FIG. 15 includes the knuckle-bend sensor in rectangle 1504, the tilt sensors TS-1 and TS-2 in rectangle 1505, and, in rectangle 1506, the plurality of touch sensors 1202 that may be selectively engaged one at a time by the THUMB sensors 1201.

Signals specifying the appropriate character are received by register 1503 each time the THUMB sensor 1201 engages one of the touch sensors 1202. The sensors associated with each character are shown on FIG. 16. Thus, the signals specifying digit 0 are generated and stored in register 1503 when the THUMB sensor engages sensor 16 while the tilt sensor (TS-2) is activated. Signals specifying the character "Y" are generated when the THUMB sensor engages sensor 9 while the knuckle-bend sensor (KBS) and the tilt sensor (TS-1) are activated. The character "z" is generated when the THUMB sensor engages touch sensor 10 while the tilt sensor (TS-1) is activated. The other characters that may be generated by the embodiment shown on FIGS. 12, 13, and 14, together with the sensors that must be active for each such character, may be determined from an analysis of FIG. 16.

Flip-flop 1508 is provided to advise the processor 1500 whenever the register 1503 has new and valid data. Normally, the flip-flop 1508 is reset by the processor. However, the touching of the THUMB sensor 1201 to any of the touch sensors 1202 applies a signal through OR gate 1507 to set flip-flop 1508. This applies a true signal from its Q output to the processor to advise it that the register now contains new and valid data. The processor then resets the flip-flop, scans the register, receives this data, stores it in its RAM memory, and then outputs this data from its memory to output device 1510 in ASCII form.

What is claimed is:

1. A man-machine interface for translating discrete character specifying positions of a hand into electrical signals representing said characters comprising:

flex sensors positioned with respect to said hand for detecting the flexing of associated digit joints, contact sensors positioned with respect to the digits of said hand and adapted so that a selected pair of contact sensors contact each other as said hand assumes different character specifying positions, additional sensors positioned with respect to the digits and metacarpus of said hand for detecting hand movements, means including said flex sensors and said contact sensors and said additional sensors responsive as said hand assumes different character specifying positions for generating electrical signals representing each of said specified characters, and means responsive to said electrical signals from said sensors as said hand assumes said different character specifying positions for applying output signals identifying each of said specified characters to a utilization device.

2. The interface of claim 1 in which said additional sensors include:
a sensor responsive to the movements of said hand for generating output signals specifying the current position of said hand with respect to a predetermined plane of reference.

3. The interface of claim 2 in which said additional sensors further include:
a sensor responsive to the movements of said hand for generating output signals specifying the current position of said hand with respect to the gravitational vector.

4. The interface of claim 3 in which said additional sensors further include:
a mode sensor positioned with respect to said hand, said mode sensor being responsive to a predetermined hand motion for generating output signals indicating whether subsequent hand positions represent numbers or alphabet characters, and
means responsive to the receipt of a mode signal for translating subsequently received hand position signals into output signals representing numbers or alphabet characters under control of said priorly received mode signal.

5. The interface of claim 4 in which said additional sensors further include:
a clock sensor positioned with respect to said hand, said clock sensor being responsive to a predetermined hand movement for generating an output signal that causes the character associated with a priorly formed hand position to be transmitted to said utilization device.

6. The interface of claim 5 in combination with:
a hand covering means, said covering means adapted to receive the hand of a user of said interface, and
means for affixing said sensors to said covering means.

7. The interface of claim 5 or 6 in combination with:
a data register, means for applying said sensor output signals to said register, a data processor,
means for applying to said processor said signals stored in said register under control of a signal applied from said clock sensor to said processor independent of said register,
said processor being responsive to the receipt of said sensor signals for identifying each specified character, and
said processor being further responsive to the receipt of said sensor signals for transmitting output signals identifying each specified character to said utilization device.

8. A method of translating discrete character specifying positions of a user's hand into electrical signals representing said specified characters, said method comprising the steps of:
(1) associating the phallanges of said hand with contact sensors adapted so that a different pair of said contact sensors contact each other as said user's hand assumes said different character specifying positions,
(2) associating at least one joint of said hand with a flex sensor for detecting the flexing of the associated joint as the hand assumes certain ones of said character specifying positions, (3) associating additional sensors with respect to said hand for detecting hand movements as said user's hand assumes said different character specifying positions,
(4) combinationally actuating said sensors as said user's hand assumes different character specifying positions,
(5) generating under control of said actuated sensors electrical signals representing said specified characters, and
(6) applying said generated signals to a data utilization device.

9. The method of claim 8 wherein said additional sensors include:
sensors positioned with respect to the metacarpus portion of said hand for generating output signals specifying the current position of said hand with respect to a predetermined plane of reference.

10. The method of claim 9 wherein said additional sensors further include:
a sensor positioned with respect to said hand for generating output signals specifying the position of said hand with respect to the gravitational vector.

11. The method of claim 10 wherein said additional sensors further include:
a mode sensor for specifying whether subsequently formed hand positions represent numbers or alphabet characters.

12. The method of claim 11 wherein said additional sensors further include:
a clock sensor, said clock sensor being responsive to a predetermined hand movement for generating an output signal that effects the transmission of said signals representing said formed characters to said data utilization device.

13. The method of claim 8, or 12 in combination with the steps of:
(1) applying said signals from said sensors to a register,
(2) applying said signals in said register to a processor,
(3) translating said signals received by said processor into output signals identifying each formed character, and
(4) applying said output signals from said processor to said data utilization device.

14. A man-machine interface for translating discrete character specifying positions of a hand into electrical signals representing said characters comprising:
flex sensor means positioned with respect to said hand for generating said electrical signals in response to the flexing of the digit joints on the phallanges,
contact sensor means positioned with respect to said hand for generating said electrical signals in response to the contact between selected ones of the digits or between selected ones of the digits and the metacarpus,
a first tilt sensor means positioned with respect to said hand for generating said electrical signals in response to the movement of said hand through a horizontal plane of reference as said hand assumes different ones of said character specifying positions,
a second tilt sensor means positioned with respect to said hand for generating said electrical signals in response to the movement of said hand through a gravitational vector as said hand assumes different ones of said character specifying positions, a first inertial sensor means positioned with respect to said hand for generating said electrical signals in response to the twisting of said hand or wrist or arm as said hand assumes different ones of said character specifying positions, a second inertial sensor means positioned with respect to said hand for generating said electrical signals in response to the flexing of said hand or wrist as said hand assumes different ones of said character specifying positions, and means responsive to said electrical signals from said sensors as said hand assumes said different character specifying positions for applying output signals identifying said specified characters to a data utilization device.

15. The interface of claim 14 in combination with:

a transmitting means connected to said sensors for transmitting said electrical signals from said sensors to a data register, a storing means in said data register for storing said electrical signals from said sensors, an applying means connected to said storing means for applying said electrical signals in said data register to a processor, a translating means for translating said electrical signals received by said processor into output signals identifying each formed character specifying position, and a second transmitting means for transmitting said output signals from said processor to said data utilization device.

16. The interface of claim 15 in combination with:

an individual digit and metacarpus covering means for receiving said hand of a user, and an affixing means for attaching said sensors to said covering means.

17. A man-machine interface for translating discrete character specifying positions of a hand into electrical signals representing said characters comprising:

a first flex sensor means positioned between the distal and middle phalanx portion of the phallanges for generating said electrical signals in response to the flexing of the distal phallange joints, a second flex sensor means positioned between the middle and proximal phalanx portion of the phallanges for generating said electrical signals in response to the flexing of the middle phallange joints, a third flex sensor means positioned between the proximal phalanx and the metacarpus portion of said hand for generating said electrical signals in response to the flexing of the proximal phallanges joint, a first contact sensor means positioned with respect to the tip of the distal portion of the first and third and fifth phallanges for generating said electrical signals in response to the contact between selected ones of the phallanges or between selected ones of the phallanges and the metacarpus, a second contact sensor means positioned with respect to the distal portion of the second and third and fourth and fifth phallanges for generating said electrical signals in response to the contact between selected ones of the phallanges or between selected ones of the phallanges and the metacarpus, a third contact sensor means positioned with respect to the middle portion of the second and third and fourth and fifth phallanges for generating electrical signals in response to the contact between selected ones of the phallanges or between selected ones of the phallanges and the metacarpus, a fourth contact sensor means positioned with respect to the proximal portion of the second and third and fourth and fifth phallanges for generating electrical signals in response to the contact between selected ones of the phallanges or between selected ones of the phallanges and the metacarpus, a first tilt sensor means positioned with respect to the distal portion of the first phallange for generating electrical signals in response to movement of said hand through the horizontal plane of reference as said hand assumes different ones of said different character specifying positions, a second tilt sensor means positioned with respect to the metacarpus portion of said hand for generating electrical signals in response to the movement of said hand through the gravitational vector as said hand assumes different ones of said different character specifying positions, a clock sensor means positioned with respect to the back portion of the metacarpus of said hand for generating electrical signals in response to the twisting motion of said hand or wrist or arm as said hand assumes different ones of said different character specifying positions, a mode sensor means positioned with respect to the back portion of the metacarpus of said hand for generating said electrical signals in response to the flexing motion of said hand or wrist as said hand assumes said different character specifying positions, means responsive to said electrical signals from said sensors as said hand assumes said different character specifying positions for applying output signals identifying said specified characters to a data utilization device.

18. The interface of claim 17 in combination with:

a transmitting means connected to said sensors for transmitting said electrical signals from said sensors to a data register, a storing means in said data register for storing said electrical signals from said sensors, an applying means connected to said storing means for applying said electrical signals under control of a signal applied from said clock sensor at the conclusion of each of said character specifying positions to a processor, an applying means connected to said storing means for applying said electrical signals under control of a signal applied from said mode sensor independent of said data register wherein subsequent character specifying positions indicate numbers or alphabet characters to a processor, a translating means for translating said electrical signals received by said processor into output signals identifying each formed character specifying position, and a second transmitting means for transmitting said output signals from said processor to said data utilization device.

19. The interface of claim 18 in combination with:

an individual phallange metacarpus and wrist covering means for receiving said hand of a user, and an affixing means for attaching said sensors to said covering means.

* * * * *